(12) United States Patent
Lynch

(10) Patent No.: US 6,177,070 B1
(45) Date of Patent: Jan. 23, 2001

(54) DEODORANT COMPOSITION

(76) Inventor: Una E. Lynch, 515 S. Lexington Pkwy., St. Paul, MN (US) 55116

(*) Notice: Under 35 U.S.C. 154(b), the term of this patent shall be extended for 0 days.

(21) Appl. No.: 09/225,752

(22) Filed: Jan. 5, 1999

Related U.S. Application Data

(60) Provisional application No. 60/070,401, filed on Jan. 5, 1998.

(51) Int. Cl.$^7$ ...................................................... A61L 9/01

(52) U.S. Cl. ........................ 424/76.1; 424/76.2; 424/76.3; 424/76.4; 424/76.5; 424/76.8; 424/405

(58) Field of Search .................................. 424/76.1–76.5, 424/405, 76.8, 489

(56) References Cited

U.S. PATENT DOCUMENTS

| | | | |
|---|---|---|---|
| 4,078,050 | 3/1978 | Hart | 424/76 |
| 4,315,945 * | 2/1982 | Sprecker | 426/3 |
| 5,776,453 | 7/1998 | Van Den Elshout | 424/65 |
| 5,795,566 | 8/1998 | Joulain et al. | 424/76.1 |

* cited by examiner

Primary Examiner—S. Mark Clardy
Assistant Examiner—Kathryne E. Shelborne
(74) Attorney, Agent, or Firm—Kinney & Lange, P.A.

(57) ABSTRACT

Improved deodorants for offensive odors are made by combinations in a suitable solvent or carrier of at least two aldehydes, preferably in the form of addition components, with at least one unsaturated compound. These combinations can be further improved by the addition of other ingredients such as acidic or basic compounds, antioxidants, surfactants, chelating agents, and antimicrobial agents.

16 Claims, No Drawings

DEODORANT COMPOSITION

This application claims benefit of Provisional application Ser. No. 60/070,401 Jan. 5, 1998.

BACKGROUND OF THE INVENTION

Most deodorants now in use to combat or eliminate malodors contain substances with powerful and persistent odors which essentially mask the obnoxious odor. However, many people find these odors objectionable, so that an object of this invention is to formulate deodorants compositions that would quickly deodorize offensive odors and leave the environment essentially odorless.

BRIEF SUMMARY OF THE INVENTION

The present invention includes a deodorant composition composed of at least two different aldehydes in the form of addition products and an unsaturated organic compound. Preferably, the addition compounds are a hemiacetal or an acetal of an alcohol or glycol.

DETAILED DESCRIPTION

A feature of the present invention resides in the provision of deodorant compositions which rapidly eliminate or greatly reduce offensive odors leaving no persistent odor of their own. Previously I had found that various lower alkyl or aryl substituted 6-hydroxy-1,3-dioxanes serve as effective deodorants and that their deodorant action against certain odors is increased in mildly acidic or mildly basic media (U.S. Pat. No. 4,078,050). The substituted dioxanes described in this earlier patent are trimers of aldehydes that are in equilibrium with their monomers. As trimers, the aldehyde groups are stabilized and protected from air oxidation.

I have since discovered that improved deodorants for offensive odors can be made by combining at least two different aldehydes, preferably in the form of their addition products, in a suitable vehicle or carrier with at least one volatile unsaturated compound. Both aldehydes are preferably in the form of a hemiacetal or acetal of an alcohol or glycol, thereby increasing the efficacy of the deodorant composition.

The preferred aldehydes are formaldehyde, acetaldehyde, glyoxal, 2-hydroxybutanal, glutaraldehyde, or benzaldehyde. The preferred alcohols and glycols are methanol, ethanol, isopropanol, propylene glycol, triethylene glycol or hexylene glycol. Each addition product of the present invention is formed from a different aldehyde. One alcohol or glycol may be chosen to react with each different aldehyde.

In the special case of formaldehyde, a number of different addition products can also be formed with nitromethane, bromonitromethane, or urea and used, such as tris(hydroxymethyl)nitromethane, 2-bromo-2-nitro-1,3-propanediol, dimethyloldimethylhydantoin, and substituted oxazolidines.

All of the addition products of the present invention are in equilibrium with their component compounds, so that in the presence of a malodor which reacts with the free aldehyde, more of the addition compound will revert to the aldehyde form. Also, the addition products tend to prevent all of the chosen aldehydes from oxidizing and provide a reservoir of aldehyde for reaction with the malodor. Furthermore, these addition compounds also have the advantage of reducing the odor of the aldehyde.

The other essential component of these deodorants is at least one unsaturated compound. The preferred unsaturated compounds are usually the more volatile components of an essential oil or flavoring. The preferred compounds are citral, geraniol, ionone, limonene, linalool and linalyl acetate. Because these unsaturated compounds are reactive molecules and subject to air oxidation, another feature of the present invention resides in the provision of a nonvolatile antioxidant oxidant, such as ascorbic acid or its sodium salt, butylated hydroxyanisole, butylated hydroxytoluene and alpha-tocopherol.

A further feature of the present invention resides in the provision of deodorant compositions of the types described which in their preferred forms contain a surfactant or wetting agent. The purposes of the surfactant are to increase the rates at which the deodorant solutions penetrate sources of odors in order to speed up the rates of deodorization and to aid in the removal of any residual materials from fabrics, rugs and floors. The amount of surfactant would normally be small, but larger amounts of surfactants could be used to prepare solutions for deodorizing pets who have encountered a skunk or rolled in dead fish or the like.

An added feature of the present invention resides in the provision of deodorants of the types described which in their preferred forms contain a chelating agent to aid in stain removal.

Another feature of the present invention resides in the provision of deodorants of the types described, which in their preferred forms contain an antimicrobial agent which will aid in the deodorization process by inhibiting the growth of microorganisms and thereby reduce the formation of odoriferous products by them. The dioxane compounds themselves are found to exhibit antimicrobial action, but other antimicrobial agents may be added for greater effectiveness. The addition products of formaldehyde, where used, will also contribute to antimicrobial activity. Among the preferred antimicrobial agents are sodium benzoate, sodium propionate, dialkyl ($C_8$–$C_{18}$) dimethyl ammonium chloride, and salts of undecylenic acid.

The deodorant mixture of compounds is best applied from a solution or suspension in a volatile liquid vehicle. Water is a preferred vehicle, but organic solvents may be used in whole or in part where desired for greater solubility of the organic components.

These deodorants are designed to be sprayed directly on the source of the malodor and thus prevent any further odor formation. The active components of these deodorant formulations are volatile so that some deodorant will be released into the air on spraying the source of the malodor thus deodorizing the malodor already present in the ambient air.

I have discovered that these improved formulations are even more effacious in reducing or eliminating unpleasant odors associated with excreta, pets, necrotic tissue and skunks than those described in my previous patent. Spraying the inside of the toilet before use eliminates fecal odor or defecation. Similarly, they are useful to deodorize odoriferous diapers, incontinent pads and bedpans. For deodorization of ostomy bags a more concentrated formulation can be made and added dropwise to bags before use.

Application on cat litter eliminates the unpleasant odors which can build up in cat boxes. These formulations may be also used on furniture, carpeting and flooring contaminated with excreta. For example, they have the advantage of eliminating urine odors so that the animal does not return to the same place to urinate. In veterinarians' offices, the use of these deodorants on baseboards, carpeting and flooring reduces the incidence of urination by dogs and cats. Pets will often urinate in an area where the odor of urine is detected, but apparently are reluctant to do so if urine odor is not detected.

In veterinary medicine and mortuary science, these deodorants are useful for deodorizing necrotic tissue. They are also effective in greatly reducing or eliminating the odor of skunk from pets, cars, camping equipment and the like.

The mildly acid formulations in the lower concentrations can be applied to the genital and anal area of tom cats to control their offensive odor. Similarly, the application of these acidic deodorants three or four times daily to the genital areas of bitches in heat greatly reduces this odor so that their attraction to male dogs is greatly diminished. Application of these deodorants to pets who have rolled in dead fish or encountered a skunk controls these offensive odors also.

The mildly alkaline deodorant formulations in the lower concentrations are also useful in deodorizing dog body odor by applying the deodorant to facial folds, ears, genital and anal areas using a cloth wet with the deodorant.

The alkaline deodorant formulations are also effective against human perspiration odor. Laundering washable clothing removes perspiration odor, but dry cleaning does not. These formulations are therefore useful to deodorize nonwashable clothing, especially costumes and uniforms, shoes, athletic equipment and prosthetic devices which smell of perspiration.

Used on leather, the alkaline deodorant formulations have the added advantage of conditioning it. Perspiration soaked leather hardens and becomes somewhat brittle. Application of these types of deodorants returns the leather to its naturally soft and pliable condition.

Both of the mildly acidic and alkaline formulas in lower concentrations have been tested for skin and eye irritation and found to be nonirritating by an independent laboratory. Similarly, these formulations have also been tested for dermal sensitization by the same laboratory with negative results.

The preferred ranges of the components of these deodorants for some typical applications are given by the following tables.

TABLE 1

COMPONENT COMPOSITION RANGES FOR ANIMAL EXCRETA DEODORANTS

| PERCENTAGE BY WEIGHT | COMPONENT |
| --- | --- |
| 0–0.8 | Alkoxylated fatty alcohol (PPG-8-pareth-28-11) |
| 0–0.5 | Benzaldehyde |
| 0–0.4 | 1,3-Bis(hydroxymethyl)-5,5-dimethylhydantoin with 5% 3-iodo-2-propynyl butyl carbamate |
| 0–1.0 | 2-Bromo-2-nitro-1,3-propanediol |
| 0–1.0 | (Ethylenedinitrilo) tetraacetic acid, tetrasodium salt |
| 0–0.5 | Citral |
| 0–3.0 | Citric acid |
| 0–0.4 | Dimethylol dimethyl hydantoin |
| 0–0.5 | 2,4 Di(alkyl or aryl)-6-hydroxy-1,3-dioxane |
| 0–2.0 | Ethanol (95%) |
| 0–0.3 | Geraniol |
| 0–0.4 | Glutaraldehyde (50% aqueous) |
| 0–2.5 | Glyoxal (40% aqueous) |
| 0–0.5 | 2-Hydroxybutanal |

TABLE 1-continued

COMPONENT COMPOSITION RANGES FOR ANIMAL EXCRETA DEODORANTS

| PERCENTAGE BY WEIGHT | COMPONENT |
| --- | --- |
| 0–0.2 | Ionone |
| 0–3.0 | Isopropanol |
| 0–3.0 | Lactic acid (85% aqueous) |
| 0–2.0 | Limonene |
| 0–0.5 | Linalool |
| 0–2.0 | Methanol |
| 0–0.5 | Nonionic surfactant |
| 0–0.3 | Perfume oil |
| 0–5.0 | Phosphoric acid, (75% aqueous) |
| 0–2.0 | POE(20)isocetyl ether |
| 0–3.5 | Propylene glycol |
| 0–1.5 | Polysorbate 20 |
| 0–9.0 | Sodium dihydrogen phosphate |
| 0–4.0 | Tartaric acid |
| 0–3.0 | Triethylene glycol |
| 0–3.0 | Tris(hydroxymethyl)nitromethane (50% aqueous) |
| q.s. to 100 | Water |

TABLE 2

COMPONENT COMPOSITION RANGES FOR HUMAN EXCRETA DEODORANTS

| PERCENTAGE BY WEIGHT | COMPONENT |
| --- | --- |
| 0–2.0 | Alkoxylated fatty alcohol (PPG-8-pareth-28-11) |
| 0–0.5 | Benzaldehyde |
| 0–0.4 | 1,3-Bis(hydroxymethyl)-5,5-dimethylhydantoin with 5% 3-iodo-2-propynyl butyl carbamate |
| 0–0.3 | Citral |
| 0–1.5 | Citric acid |
| 0–0.5 | 2,4-Dimethyl-6-hydroxy-1,3-dioxane |
| 0–0.5 | 2,4-Di(alkyl or aryl)-6-hydroxy-1,3-dioxane |
| 0–3.0 | Ethanol (95%) |
| 0–0.4 | Geraniol |
| 0–0.2 | Glutaraldehyde (50% aqueous) |
| 0–2.0 | Glyoxal (40% aqueous) |
| 0–0.4 | 2-Hydroxybutanal |
| 0–3.0 | Isopropanol |
| 0–0.2 | Ionone |
| 0–1.6 | Lactic acid (85% aqueous) |
| 0–0.6 | Limonene |
| 0–2.0 | Methanol |
| 0–0.2 | Nonionic surfactant |
| 0–0.2 | Perfume oil |
| 0–1.4 | Phosphoric acid (75% aqueous) |
| 0–2.3 | Polysorbate 20 |
| 0–3.5 | POE(20)isocetyl ether |
| 0–3.5 | Propylene glycol |
| 0–9.0 | Sodium dihydrogen phosphate |
| 0–4.0 | Tartaric acid |
| 0–3.0 | Triethylene glycol |
| 0–2.0 | Tris(hydroxymethyl)nitromethane (50% aqueous) |
| q.s. to 100 | Water |

TABLE 3

COMPONENT COMPOSITION RANGES FOR OSTOMY DEODORANT

| PERCENTAGE BY WEIGHT | COMPONENT |
| --- | --- |
| 0–1.0 | Alkoxylated fatty alcohol (PPG-8-pareth-28-11) |
| 0–1.0 | Benzaldehyde |
| 0–1.0 | Boric acid |
| 0–10.0 | Citric acid |
| 0–0.5 | 2,4-Dimethyl-6-hydroxy-1,3-dioxane |
| 0–0.5 | 2,4-Dialkyl or aryl-6-hydroxy-1,3-dioxane |
| 0–2.0 | Glutaraldehyde, (50% aqueous) |
| 0–5.0 | Glyoxal, (40% aqueous) |
| 0–1.0 | 2-Hydroxybutanal |
| 0–2.0 | Limonene |
| 0–2.0 | Linalool |
| 0–1.0 | Nonionic surfactant |
| 0–0.2 | Retinol |
| 0–6.7 | Phosphoric acid, (75% aqueous) |
| 5.0–30.0 | Propylene glycol |
| 0–8.0 | Sodium monophosphate |
| 0–0.5 | Alpha-tocopherol |
| 0–20.0 | Triethylene glycol |
| 0–10.0 | Tris(hydroxymethyl)nitromethane (50% aqueous) |
| q.s. to 100 | Water |

TABLE 4

COMPONENT COMPOSITION RANGES FOR PERSPIRATION AND DOG BODY ODOR DEODORANTS

| PERCENTAGE BY WEIGHT | COMPONENT |
| --- | --- |
| 0–0.2 | Alkoxylated fatty alcohol (PPG-8-pareth-28-11) |
| 0–0.4 | Benzaldehyde |
| 0–0.4 | 1,3-Bis(hydroxymethyl)-5,5-dimethylhydantoin with 5% 3-iodo-2-propynyl butyl carbamate |
| 0–0.4 | Dialkyldimethylammonium chloride |
| 0–0.4 | 2,4-Dimethyl-6-hydroxy-1,3-dioxane |
| 0–0.4 | 2,4-Di(alkyl or aryl)-6-hydroxy-1,3-dioxane |
| 0–6.0 | Disodium phosphate |
| 0–2.0 | Ethanol (95%) |
| 0–1.5 | Ethylenediaminetetraacetic acid, tetra-sodium salt |
| 0–0.3 | Glutaraldehyde (50% aqueous) |
| 0–1.5 | Glyoxal (40% aqueous) |
| 0–2.0 | Hexylene glycol |
| 0–0.2 | 2-Hydroxybutanal |
| 0–2.0 | Isopropanol |
| 0–0.6 | Limonene |
| 0–0.2 | Linalool |
| 0–0.3 | Linalyl acetate |
| 0–1.5 | Methanol |
| 0–1.0 | Nonionic surfactant |
| 0–0.15 | Perfume oil |
| 0–3.0 | POE(20)isocetyl ether |
| 0–1.7 | Polysorbate 20 |
| 0–6.5 | Potassium bicarbonate |
| 0–0.2 | Potassium undecylenate |
| 0–3.5 | Propylene glycol |
| 0–2.0 | Sodium benzoate |
| 0–2.0 | Sodium borate |
| 0–2.5 | Sodium carbonate |
| 0–2.6 | Sodium propionate |
| 0–3.0 | Triethylene glycol |
| q.s. to 100 | Water |

The following examples are not intended to limit the present invention in anyway.

EXAMPLES

In the following examples set forth below, each aldehyde was first mixed with an alcohol or glycol to obtain the addition product. Once the two aldehydes and the glycol or alcohol were mixed, the remaining ingredients where then added.

Example 1
5.0 g. Monosodium phosphate
0.5 g. 2,4-Dimethyl-6-hydroxy-1,3-dioxane
2.0 g. 1,2-Dimethoxyethylene glycol
0.2 g. Geraniol
92.3 g. Water Example 2
3.0 g. Citric acid
2.0 g. Tris (hydroxymethyl) nitromethane (50% aqueous)
1.5 g. 1,5-Diethoxy-1,5-pentanediol
0.3 g. Limonene
1.0 g. Polyoxyethylene (20) isocetyl ether
92.2 g. Water Example 3
2.0 g. Lactic acid (85% aqueous)
0.3 g. 2,4-Diethyl-6-hydroxy-1,3-dioxane
0.4 g. 2-Bromo-2-nitropropanediol
0.5 g. Ionone
1.0 g. Sorbitan poly(20)ethyleneoxymonolaurate
95.8 g. Water Example 4
4.0 g. Tartaric acid
1.0 g. Alpha-hydroxy-alpha-ethoxytoluene
0.6 g. 4,4-Dimethyloxazolidine
0.3 g. Linalool
1.0 g. Polyoxyethylene (20) isocetyl ether
93.1 g. Water Example 5
6.0 g. Monosodium phosphate
2.5 g. Phosphoric acid (75% aqueous)
1.0 g. 1,2-Diisopropoxyethylene glycol
1.2 g. 1-Methoxy-1,3-butanediol
0.5 g. Citral
0.05 g. Butylated hydroxyanisole
0.1 g. Nonylphenoxypoly (2–12) ethyleneoxyethanol
0.2 g. Dimethylol dimethylhydantoin
88.45 g. Water Example 6
8.0 g. Monosodium phosphate
1.0 g. 1-Metboxy-1,3-butylene glycol 0.3 g. 1,5-Diethoxy-1,5-pentanediol
0.6 g. Limonene
10.0 g. Propylene glycol
1.5 g. Polyoxyethylene (20) isocetyl ether
0.1 g. PPG-8-pareth-28-11
0.4 g. 1,3-Bis (hydroxymethyl)-5,5-Dimethylhydantoin with 5% 3-iodo-2-propynylbutyl carbamate
78.1 g. Water
Example 7
3.0 g. Potassium carbonate
2.5 g. 1,2-Dimethoxyethylene glycol
1.0 g. 1,5-Diethoxy-1,5-pentanediol
0.3 g. Citral
0.1 g. 7-Ethyl bicyclooxazolidine
0.6 g. Sorbitan monolaurate
1.5 g. Sorbitan poly (20) ethyleneoxymonolaurate
91.0 g. Water
Example 8
6.0 g. Sodium bicarbonate
0.2 g. 2,4-Dimethyl-6-hydroxy-1,3-Dioxane
0.5 g. Alpha-hydroxy-alpha-methoxytoluene
0.3 g. Linalyl acetate
0.3 g. (Ethylenedinitriolo) tetraacetic acid, tetraasodium salt
1.0 g. Polyoxyethylene (20) isocetyl ether
0.8 g. Sodium propionate
0.1 g. Butylated hydroxytoluene
5.0 g. Triethylene glycol
85.8 g. Water
Example 9
5.0 g. Disodium phosphate
0.6 g. 1-gamma hydroxypropoxy-1,3-butanediol
2.0 g. Tris (hydroxymethyl) nitromethane
0.1 g. Ionone
0.1 g. Geraniol
0.05 g. Butylated hydroxyanisole
0.8 g. Sodium propionate
0.2 g. Sodium benzoate
0.5 g. Sorbitan monostearate
1.0 g. Sorbitan poly (20) ethyleneoxymonostearate
0.2 g. (Ethylenedinitrilo) tetraacetic acid, tetrasodium salt
89.45 g. Water
Example 10
5.0 g. Potassium bicarbonate
0.5 g. Alpha-hydroxy-alpha-methoxy toluene
1.5 g. 1,1,2,2-tetramethoxyethane
0.3 g. Limonene
0.2 g. Sodium ascorbate
0.1 g. 1,3-Bis (hydroxymethyl)-5,5-dimethylhydantoin with 5% 3-iodo-2-propynyl butyl carbamate
5.0 g. Triethylene glycol
3.0 g. Isopropanol
0.1 g. Nonylphenoxypoly (2–12) ethyleneoxyethanol
0.5 g. Potassium undecylenate
0.5 g. Sodium propionate
83.3 g. Water
Example 11
2.5 g. Sodium carbonate
0.4 g. 2,4-Dimethyl-6-hydroxy-1,3-dioxane
1.5 g. Tris (hydroxymethyl) nitromethane (50% aqueous)
0.2 g. Limonene
0.1 g. Ionone
0.2 g. (Ethylenedinitrilo) tetraacetic acid, tetrasodium salt
0.2 g. Sodium benzoate
0.5 g. Sodium propionate
1.0 g. PPG-80-pareth-28-11
93.3 g. Water
Example 12
6.0 g Disodium phosphate
3.0 g. 1,2-Diethoxyethylene glycol
0.6 g. 2-Bromo-2-nitro-1,3-propandiol
0.3 g. Citral
0.05 g. Butylated hydroxytoluene
0.2 g. Dialkyl ($C_8$–$C_{18}$) dimethylammonium chloride
3.5 g. Hexylene glycol
0.5 g. Polyoxyethylene (20) isocetyl ether
0.4 g. (Ethylenedinitrilo) tetraacetic acid, tetrasodium salt
5.0 g. Propylene glycol
80.45 g. Water
Example 13
4.5 g. Potassium bicarbonate
3.0 g. 1,2-Dimethoxyethylene glycol
0.5 g. Alpha-hydroxy-alpha-ethoxytoluene
0.4 g. 2,4-Dimethyl-6-hydroxy-1,3-dioxane
0.6 g. Limonene
0.4 g. (Ethylenedinitrilo) tetraacetic acid, tetraasodium salt
1.0 g. Sodium propionate
0.2 g. Sodium benzoate
1.5 g. Polyoxyethylene (20) isocetyl ether
0.1 g. PPG-8-pareth-28-11
0.2 g. Sodium undecylenate
0.1 Dialkyl ($C_8$–$C_{18}$) dimethylammonium chloride
5.0 g. Propylene glycol
3.0 g. Triethylene glycol
79.4 g. Water
Example 14
5.0 g. Citric acid
0.3 g. Maleic acid
1.0 g. Tartaric acid
2.0 g. Tris (hydroxymethyl) nitromethane
3.0 g. 1,2-Diethoxyethylene glycol
0.2 g. 1,5-Diethyl-1,5-pentanediol
0.6 g. Limonene
0.4 g. Linalool
30.0 g. Isopropanol
27.8 g. Propylene glycol
10.0 g. Triethylene glycol
10.0 g. Hexylene glycol
Example 15
2.0 g. Lactic acid (85% aqueous)
2.5 g. Phosphoric acid (75% aqueous)
1.0 g. Alpha-hydroxy-alpha-methoxytoluene
2.0 g. 2,4-Dimethyl-6-hydroxy-1,3-dioxane
0.1 g. 4-Chloro-3-methylphenol 0.3 g. Geraniol
0.2 g. Ionone
0.3 g. Linalool
1.0 g. Nonylphenoxypoly (2–12) ethyleneoxyethanol
5.0 g. Propylene glycol
10.0 g. Triethylene glycol
75.6 g. Water Example 16

6.0 g. Benzoic acid
2.0 g. Phosphoric acid (75% aqueous)
0.3 g. 2-Bromo-2-nitro-1,3-propanediol
2.0 g. Alpha-hydroxy-alpha-methoxytoluene
2.0 g. 2,4-Dimethyl-6-hydroxy-1, 3-dioxane
2.0 g. 1,5-Isopropoxy-1, 5-pentanediol
0.3 g. Citral
0.2 g. Ionone
0.4 g. Limonene
0.1 g. Octylphenoxypoly (8) ethyleneoxyethanol
30.0 g. Isopropanol
20.0 g. Triethylene glycol
10.0 g. Hexylene glycol
24.7 g. Propylene glycol Although the present invention has been described with reference to preferred embodiments, workers skilled in the art will recognize that changes may be made in form and detail without departing from the spirit and scope of the invention.

What is claimed is:

1. A deodorant composition comprising at least two different aldehydes in the form of addition compounds wherein the aldehyde group reacts with another molecule to form the addition compounds and an unsaturated organic compound.

2. The deodorant composition of claim 1 wherein the unsaturated organic compound is a component of an essential oil or flavoring.

3. The deodorant composition of claim 2 wherein the unsaturated organic compound is citral, geraniol, ionone, limonene, linalool, or linalyl acetate.

4. The deodorant composition of claim 1 and further including a nonvolatile antioxidant oxidant.

5. The deodorant composition of claim 4 wherein the antioxidant is ascorbic acid or a sodium salt thereof, butylated hydroxyanisole, butylated hydroxytoluene or alpha-tocopherol.

6. The deodorant composition of claim 1 and further including a surfactant.

7. The deodorant composition of claim 1 and further including a chelating agent.

8. The deodorant composition of claim 1 and further including an antimicrobial agent.

9. The deodorant composition of claim 1 wherein the addition compounds are formed with alcohols or glycols.

10. The deodorant composition of claim 1 wherein one of the aldehydes is formaldehyde and the addition compound is formed with nitromethane, urea or bromonitromethane.

11. The deodorant composition of claim 9 wherein the alcohols or glycols are methanol, ethanol, isopropanol, propylene glycol, triethylene glycol or hexylene glycol.

12. The deodorant composition of claim 1 wherein the aldehydes are formaldehyde, acetaldehyde, glyoxal, 2-hydroxybutanal, glutaraldehyde or benzaldehyde.

13. The deodorant composition of claim 1 wherein the addition compounds are a hemiacetal or acetal of an alcohol or glycol.

14. A method of reducing malodor, the method comprising a composition containing addition compounds derived from two different aldehydes wherein the addition compounds are formed by a reaction of the aldehyde group with another molecule intermixed within an unsaturated organic compound.

15. The method of claim 14 wherein each addition compound is formed separately and then admixed together and with the unsaturated organic compound.

16. The method of claim 14 wherein the addition product is a hemiacetal or acetal of an alcohol or glycol.

* * * * *